US00PP17452P2

(12) United States Plant Patent
Smith

(10) Patent No.: US PP17,452 P2
(45) Date of Patent: Feb. 27, 2007

(54) ***CHRYSANTHEMUM* PLANT NAMED 'YODAWN'**

(50) Latin Name: *Chrysanthemum×morifolium*
Varietal Denomination: Yodawn

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 28 days.

(21) Appl. No.: 11/157,278

(22) Filed: Jun. 21, 2005

(51) Int. Cl.
*A01H 5/00* (2006.01)

(52) U.S. Cl. ..... Plt./289; Plt./286

(58) Field of Classification Search ..... Plt./286, Plt./289

See application file for complete search history.

*Primary Examiner*—Anne Marie Grunberg
*Assistant Examiner*—S. B. McCormick-Ewoldt
(74) *Attorney, Agent, or Firm*—C. A. Whealy

(57) ABSTRACT

A new and distinct cultivar of *Chrysanthemum* plant named 'Yodawn', characterized by its compact, upright and somewhat outwardly spreading plant habit; freely branching habit; dense and full plant habit; uniform and freely flowering habit; decorative-type inflorescences with elongated oblong-shaped ray florets; yellow-colored ray florets; and natural season flowering in early September in the Northern Hemisphere.

2 Drawing Sheets

Botanical designation: *Chrysanthemum×morifolium.*
Cultivar denomination: 'Yodawn'.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yodawn'.

The new cultivar is a product of a planned breeding program conducted by the Inventor in Salinas, Calif. and Alva, Fla. The objective of the breeding program is to create new garden-type *Chrysanthemum* cultivars having inflorescences with desirable inflorescence forms, attractive floret colors and good garden performance.

The new *Chrysanthemum* originated from a cross-pollination made in February, 2002 in Salinas, Calif., of the *Chrysanthemum×morifolium* cultivar Gold Crest, disclosed in U.S. Plant Pat. No. 11,606, as the female, or seed, parent with the *Chrysanthemum×morifolium* cultivar Stephanie, disclosed in U.S. Plant Pat. No. 9,445, as the male, or pollen, parent. The new *Chrysanthemum* was discovered and selected by the Inventor as a single flowering plant within the progeny of the stated cross-pollination grown in a controlled environment in Alva, Fla. in October, 2002. The selection of this plant was based on its desirable inflorescence form, attractive floret coloration and good garden performance.

Asexual reproduction of the new cultivar by terminal vegetative cuttings in a controlled environment in Alva, Fla. since January, 2003, has shown that the unique features of this new *Chrysanthemum* are stable and reproduced true to type in successive generations.

SUMMARY OF THE INVENTION

The cultivar Yodawn has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yodawn'. These characteristics in combination distinguish 'Yodawn' as a new and distinct cultivar:

1. Compact, upright and somewhat outwardly spreading plant habit.
2. Freely branching habit; dense and full plants.
3. Uniform and freely flowering habit.
4. Decorative-type inflorescences with elongated oblong-shaped ray florets.
5. Yellow-colored ray florets.
6. Natural season flowering in early September in the Northern Hemisphere.

In side-by-side comparisons conducted in Alva, Fla., plants of the new *Chrysanthemum* differed from plants of the female parent, the cultivar Gold Crest, in the following characteristics:

1. Plants of the new *Chrysanthemum* were smaller than plants of the cultivar Gold Crest.
2. Plants of the new *Chrysanthemum* flowered about three to four days earlier than plants of the cultivar Gold Crest when grown under natural season conditions.
3. Plants of the new *Chrysanthemum* had slightly smaller inflorescences than plants of the cultivar Gold Crest.
4. Plants of the new *Chrysanthemum* flowered more uniformly than plants of the cultivar Gold Crest.

In side-by-side comparisons conducted in Alva, Fla., plants of the new *Chrysanthemum* differed from plants of the male parent, the cultivar Stephanie, in the following characteristics:

1. Plants of the new *Chrysanthemum* were slightly smaller than plants of the cultivar Stephanie.
2. Plants of the new *Chrysanthemum* and the cultiver Stephanie differed in inflorescence form as plants of the cultivar Stephanie had daisy-type inflorescences.

3. Plants of the new *Chrysanthemum* and the cultivar Stephanie differed in ray floret color as plants of the cultivar Stephanie had white-colored ray florets.

Plants of the new *Chrysanthemum* can be compared to plants of the *Chrysanthemum* cultivar Yoheidi, disclosed in U.S. Plant Pat. No. 13,830. In side-by-side comparisons conducted in Alva, Fla., plants of the new *Chrysanthemum* differed from plants of the cultivar Yoheidi in the following characteristics:

1. Plants of the new *Chrysanthemum* were slightly smaller and more mounding than plants of the cultivar Yoheidi.
2. Plants of the new *Chrysanthemum* flowered about one week later than plants of the cultivar Yoheidi when grown under natural season conditions.
3. Ray florets of plants of the new *Chrysanthemum* were slightly lighter in color than ray florets of plants of the cultivar Yoheidi.

Plants of the new *Chrysanthemum* can also be compared to plants of the *Chrysanthemum* cultivar Yellow Urano, disclosed in U.S Plant Pat. No. 13,101. In side-by-side comparisons conducted in Alva, Fla., plants of the new *Chrysanthemum* differed from plants of the cultivar Yellow Urano in the following characteristics:

1. Plants of the new *Chrysanthemum* were smaller than plants of the cultivar Yellow Urano.
2. Inflorescences of plants of the new *Chrysanthemum* had fewer disc florets than inflorescences of plants of the cultivar Yellow Urano.
3. Inflorescences of plants of the new *Chrysanthemum* were longer lasting than inflorescences of plants of the cultivar Yellow Urano.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproduction of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yodawn' grown in a container.

The photograph on the second sheet comprises a close-up view of typical inflorescences of the cultivar 'Yodawn'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canda during the late summer and early fall in an outdoor nursery under conditions and practices which approximate those generally used in commercial garden-type *Chrysanthemum* production. One cutting was planted in a 15.25-cm container in mid-July, 2004. Plants were grown under natural season conditions. During the production of the plants, temperatures ranged from 10° to 32° C. Mesurements and numerical values represent averages for typical flowering plants.

Botanical classification: *Chrysanthemum×morifolium* cultivar Yodawn.

Commercial classification: Decorative-type garden *Chrysanthemum.*

Parentage:

*Female, or seed, parent.*—*Chrysanthemum×morifolium* cultivar Gold Crest, disclosed in U.S. Plant Pat. No. 11,606.

*Male, or pollen, parent.*—*Chrysanthemum×morifolium* cultivar Stephanie, disclosed in U.S. Plant Pat. No. 9,445.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with mounded crown. Stems initially upright, then somewhat outwardly spreading; compact growth habit. Freely branching with about nine primary branches with lateral branches potentially forming at every node. Moderately vigorous.

*Plant height.*—About 22 cm.

*Plant diameter.*—About 31 cm.

*Lateral branches.*—Length: About 19 cm. Diameter: About 4 mm. Internode length: About 1.1 cm. Aspect: Upright and outwardly spreading. Texture: Pubescent. Color: 146A.

*Foliage description.*—Leaf arrangement: Alternate. Length: About 4.25 cm. Width: About 3 cm. Apex: Cuspidate. Base: Mostly truncate. Margin: Palmately lobed, sinuses mostly divergent. Texture, upper surface: Slightly pubescent. Texture, lower surface: Pubescent; veins prominent. Color: Developing and fully expanded foliage, upper surface: More green than 147A. Developing and fully expanded foliage, lower surface: More green than 147B. Venation, upper surface: More green than 147A. Venation, lower surface: Close to 147B. Petiole length: About 1.5 cm. Petiole diameter: About 3 mm. Petiole color, upper and lower surfaces: Close to 146A to 146B.

Inflorescence description:

*Appearance.*—Decorative-type inflorescence form with elongated oblong-shaped ray florets. Inflorescences borne on terminals above foliage, arising from leaf axils. Ray florets developing acropetally on a capitulum. About twelve inflorescences per lateral branch.

*Flowering response.*—Under natural season conditions, plants flower in early September in the Northern Hemisphere.

*Inflorescence bud* (*before showing color*).—Height: About 3 mm. Diameter: About 4 mm. Shape: Oblate. Color (lower surface of phyllaries): More green than 147A.

*Inflorescence size.*—Diameter: About 3.3 cm. Depth (height): About 1.4 cm. Disc diameter: About 2 mm; inconspicious. Receptacle diameter: About 4.25 mm.

*Ray florets.*—Shape: Elongated oblong. Length: About 1.6 cm. Width: About 5.5 mm. Corolla tube length: About 2 mm. Corolla tube diameter: About 1 mm. Apex: Emarginate. Margin: Fused. Texture: Smooth, glabrous; satiny. Surface: Concave to mostly flat. Orientation: Initially upright, then perpendicular to the peduncle. Number of ray florets per inflorescence: About 76 in numerous whorls. Color: When opening and fully opened, upper surface: Close to 5A. When opening and fully opened, lower surface: Close to 5C.

*Disc florets.*—Shape: Tubular, elongated. Length: About 3 mm. Width, apex: About 1 mm. Width, base: About 1 mm. Number of disc florets per inflorescence: About five. Color: Immature: Close to 9A. Mature: Apex: Close to 9A. Mid-section and base: Close to 155D.

*Phyllaries.*—Quantity per inflorescence: About 20. Length: About 6 mm. Width: About 4 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: More green than 147A.

*Peduncle.*—Length: First peduncle: About 3.8 cm. Fourth peduncle: About 4.9 cm. Diameter: About 2 mm. Strength: Strong. Aspect: About 40° from vertical. Texture: Pubescent. Color: Close to 146A.

*Reproductive organs.*—Androecium: Present on disc florets only. Anther length: Less than 1 mm. Anther color: Close to 12A. Amount of pollen: None observed. Gynoecium: Present on both ray and disc florets. Style length: About 4 mm. Style color: Close to 154A. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° to more than 38° C.

It is claimed:

1. A new and distinct cultivar of *Chrysanthemum* plant named 'Yodawn', as illustrated and described.

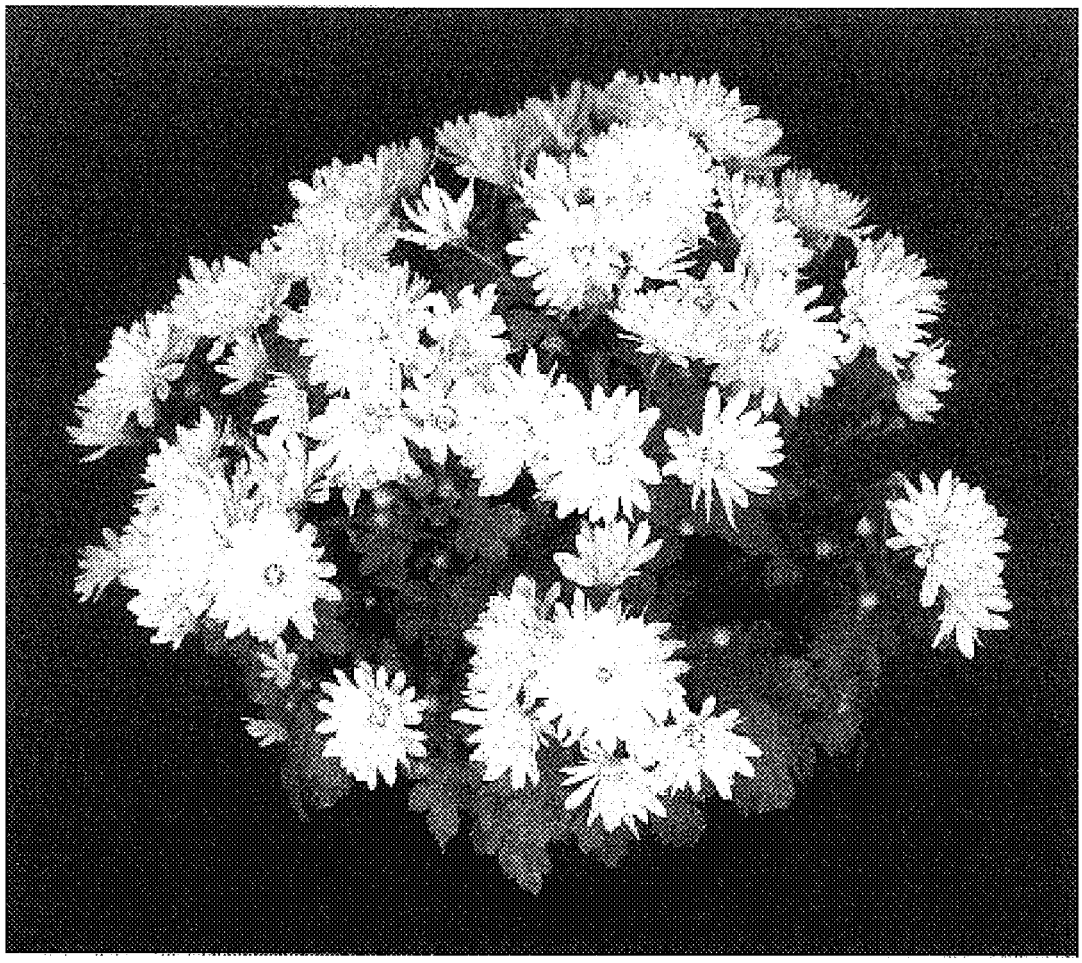

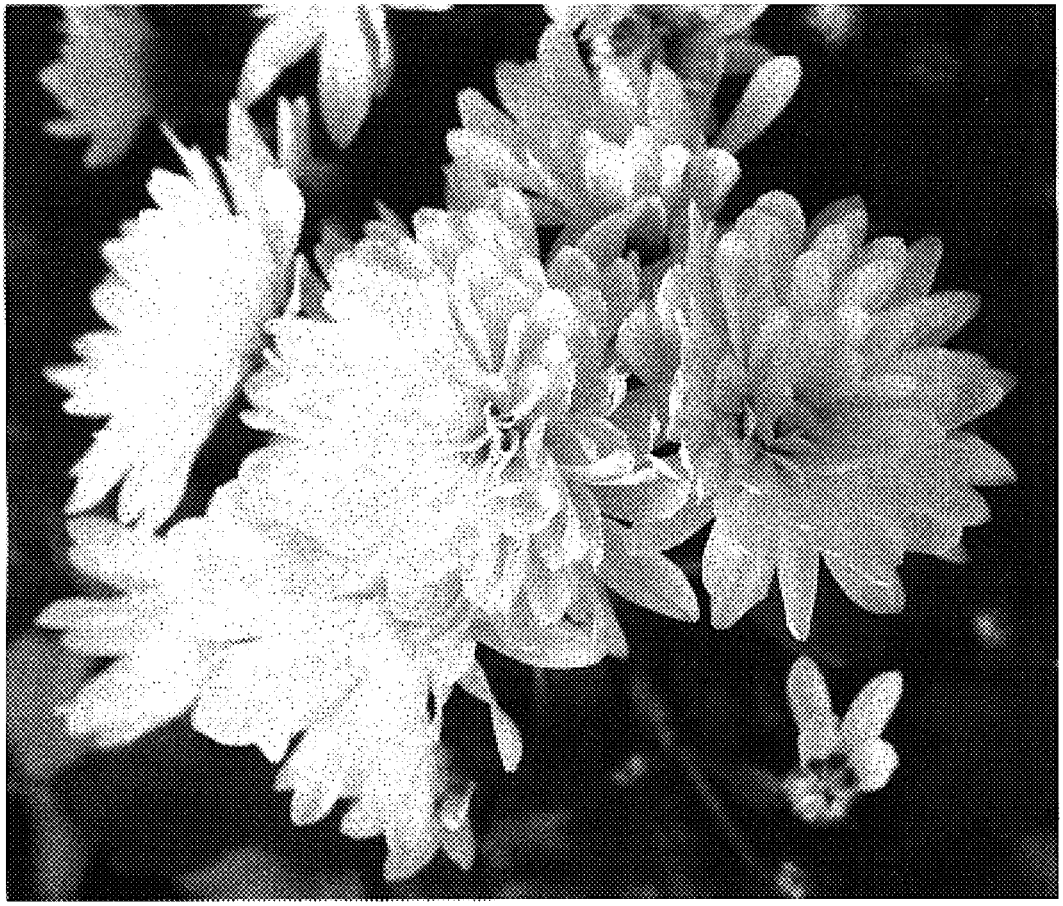

* * * * *